United States Patent [19]

Mohr et al.

[11] Patent Number: 5,846,453
[45] Date of Patent: Dec. 8, 1998

[54] PROCESS FOR PRODUCING OLIGOAMINES OR POLYAMINES

[75] Inventors: Jürgen Mohr, Grünstadt; Wolfgang Knauf, Limburgerhof; Wolf-Dieter Balzer, Ludwigshafen; Knut Oppenländer, Ludwigshafen; Wilhelmus Slotman, Ludwigshafen, all of Germany

[73] Assignee: BASF Aktiengesellschaft, Ludwigshafen, Germany

[21] Appl. No.: 809,720

[22] PCT Filed: Sep. 26, 1995

[86] PCT No.: PCT/EP95/03809

§ 371 Date: Apr. 7, 1997

§ 102(e) Date: Apr. 7, 1997

[87] PCT Pub. No.: WO96/11225

PCT Pub. Date: Apr. 18, 1996

[30] Foreign Application Priority Data

Oct. 6, 1994 [DE] Germany .......................... 44 35 688.9

[51] Int. Cl.$^6$ ................................................ B01D 17/04
[52] U.S. Cl. .................... 252/331; 252/332; 252/340; 252/344; 252/358; 528/421; 528/422; 528/492; 525/406; 525/504
[58] Field of Search .................................. 252/344, 358, 252/332, 331, 340; 528/421, 422, 492; 525/406, 540

[56] References Cited

U.S. PATENT DOCUMENTS 3,907,701  9/1975  Liebold et al. .......................... 252/344
4,147,724  4/1979  Knofel et al. ........................... 260/570
4,705,834  11/1987  Baur et al. ............................... 528/66
5,445,765  8/1995  Elfers et al. ............................ 252/344

*Primary Examiner*—Randy Gulakowski
*Attorney, Agent, or Firm*—Oblon, Spivak, McClelland, Maier & Neustadt, P.C.

[57] ABSTRACT

The preparation of alkoxylates of oligoamines or polyamines by a two-stage procedure where, in the first stage, one molecule of alkylene oxide per NH group is added onto the oligoamines or polyamines in the presence of water, alcohols or acids or a mixture thereof in the absence of a neutral or basic catalyst and, in the second stage, after removal of water and acids reaction with further alkylene oxide is carried out in the presence of a conventional neutral or basic catalyst, entails, before the second stage is carried out, an organic solvent or diluent or a mixture thereof from the group of (a) alcohols and phenols and their alkoxylates,
(b) polyalcohols based on ethylene oxide, propylene oxide, butylene oxide or a mixture thereof,
(c) N-substituted carboxamides,
(d) alkanolmonoamines and alkanolpolyamines and their alkoxylates,
(e) other alkoxylates of oligoamines or polyamines,
(f) aromatic hydrocarbons,
(g) aliphatic hydrocarbons,
(h) ethers and
(i) sulfones or sulfoxides being added.

6 Claims, No Drawings

PROCESS FOR PRODUCING OLIGOAMINES OR POLYAMINES

This application is a 371 of PCT/EP95/03809 filed Sep. 26, 1995.

BACKGROUND OF THE INVENTION

1. Field of the Invention

The present invention relates to an improved process for preparing alkoxylates of oligoamines or polyamines by a two-stage procedure where, in the first stage, one molecule of alkylene oxide per NH group is added onto the oligoamines or polyamines in the presence of water, alcohols or acids or a mixture thereof in the absence of a neutral or basic catalyst and, in the second stage, after removal of water and acids reaction with further alkylene oxide is carried out in the presence of a conventional neutral or basic catalyst.

2. Description of the Background Art

DE-B 22 27 546 discloses a two-stage process for preparing alkoxylated polyalkyleneimines in which, in the first stage, a polyalkylenepolyamine is exposed, in the presence of from 1 to 50% by weight of water, to sufficient alkylene oxide for the corresponding amino alcohol to be produced with saturation of all the valencies bonding hydrogen atoms to the nitrogen atoms and, in the second stage, after removal of the water an alkaline catalyst is added, followed by further alkoxylation.

It is known that the further reaction of the amino alcohol in the second stage must be carried out in the absence of water, because otherwise there is excessive formation of many unwanted byproducts with a glycol or polyglycol structure. However, further alkoxylation of pure polymeric amino alcohol, for example in the melt, takes place only very slowly. In particular, states of high viscosity occur at the start of this further reaction and are difficult to control and overcome, which leads to great variations in the reaction times and products which differ greatly in their viscosity.

SUMMARY OF THE INVENTION

It is an object of the present invention to find reaction conditions under which the polymeric amino alcohols from the first stage of the described preparation process can be alkoxylated in an economic and efficient manner with short reaction times to give reproducible products.

We have found that this object is achieved by a process as defined at the outset, wherein, before the second stage is carried out, an organic solvent or diluent or a mixture thereof from the group of (a) alcohols and phenols and their alkoxylates,
(b) polyalcohols based on ethylene oxide, propylene oxide, butylene oxide or a mixture thereof,
(c) N-substituted carboxamides,
(d) alkanolmonoamines and alkanolpolyamines and their alkoxylates,
(e) other alkoxylates of oligoamines or polyamines,
(f) aromatic hydrocarbons,
(g) aliphatic hydrocarbons,
(h) ethers and
(i) sulfones or sulfoxides is added.

DETAILED DESCRIPTION OF THE INVENTION

Said solvent or diluent is preferably added in an amount of from 2 to 400 parts by weight, in particular 5 to 200 parts by weight, especially 10 to 100 parts by weight, based on the weight of the adduct from the first stage.

Examples of suitable alcohols and phenols or their alkoxylates (a) are $C_1$–$C_8$-alkanols, in particular $C_1$–$C_4$-alkanols, such as ethanol, ethanol, n-propanol, isopropanol, n-butanol, isobutanol, sec-butanol, tert-butanol, n-pentanol, n-hexanol, n-heptanol, n-octanol or 2-ethylhexanol, cyclohexanol, benzyl alcohol, polyhydric alcohols such as ethylene glycols or propylene glycol, phenols such as unsubstituted phenol, cresols or naphthols and, especially in the case of phenols, products of the reaction thereof with from 1 to 30 mol, in particular 2 to 15 mol, per hydroxyl group of ethylene oxide, propylene oxide, butylene oxide or a mixture thereof.

Examples of polyglycols (b) are diethylene glycol, triethylene glycol, tetraethylene glycol and polyethylene glycols with average molecular weights of from 200 to 2000, in particular 300 to 1000, furthermore dipropylene glycol, tripropylene glycol, tetrapropylene glycol and polypropylene glycols with average molecular weights of from 270 to 2000, in particular 350 to 1000, and furthermore dibutylene glycol, tributylene glycol, tetrabutylene glycol and polybutylene glycols with average molecular weights of from 320 to 2000, in particular 400 to 1000.

Particularly suitable N-substituted open-chain or cyclic carboxamides (c) are N,N-dimethylformamide, N,N-dibutylformamide, N,N-dimethylacetamide and N-methylpyrrolidone.

Examples of suitable alkanolmono- and -polyamines or their alkoxylates (d) are monoethanolamine, diethanolamine, triethanolamine, mono-n-propanolamine, di-n-propanolamine, tri-n-propanolamine, monoisopropanolamine, diisopropanolamine, triisopropanolamine, tetraethanolethylenediamine or tetraethanolpropylenediamine and the products of the reaction thereof with from 1 to 30 mol, in particular 2 to 15 mol, per hydroxyl group of ethylene oxide, propylene oxide, butylene oxide or a mixture thereof.

Other alkoxylates of oligo- or polyamines (e) mean products of the type of the alkoxylates prepared according to the invention but which are different from the latter and must be added separately.

Particularly suitable aromatic hydrocarbons (f) are benzene, toluene, xylene, mesitylene, styrene, indane, indene and industrial aromatic cuts which consist predominantly or exclusively of aromatic hydrocarbons of these types, eg. naphtha (a mixture of alkylbenzenes) and heavy solvent naphtha. Xylene is of particular interest, this meaning both the isomerically pure o-, m- and p-xylenes and the technical mixture thereof.

Examples of aliphatic hydrocarbons (g) are pentane, hexane, heptane, cyclopentane, cyclohexane and industrial aliphatic cuts which consist predominantly or exclusively of aliphatic hydrocarbons of these types, eg. petroleum ethers boiling in the range from 35° C. to 110° C.

Particularly suitable open-chain or cyclic ethers (h) with one or more, preferably one or two, ether functionalities are diethyl ether, di-n-propyl ether, diisopropyl ether, di-n-butyl ether, methyl tert-butyl ether, dimethoxyethane, tetrahydropyran, tetrahydrofuran and dioxane.

Examples of open-chain or cyclic sulfones or sulfoxides (i) are dimethyl sulfone, diethyl sulfone, sulfolane, 3-sulfolene and dimethyl sulfoxide.

The preferred solvents and diluents to be employed according to the invention are derived from groups (b), (c), (d), (f) and (h).

Particularly suitable oligo- or polyamines to be alkoxylated by the process according to the invention are polyalkylenepolyamines with 3 to 10, preferably 3 to 7, nitrogen atoms per molecule, such as diethylenetriamine, triethylenetetramine or tetraethylenepentamine, furthermore polyvinylamines with a weight average molecular weight of from 600 to 10,000,000, preferably 2000 to 7,000,000, and furthermore polyethyleneimines with a weight average molecular weight of from 2000 to 50,000, preferably 5000 to 25,000.

Suitable for the alkoxylation according to the invention are all conventional 1,2-alkylene oxides, in particular ethylene oxide, propylene oxide and butylene oxide, it being possible to use both 1,2- and 2,3-butylene oxide, as well as styrene oxide and cyclohexene oxide, and a mixture of said alkylene oxides.

The two-stage alkoxylation process according to the invention which is set forth in the preamble is carried out in a conventional way. In the first stage thereof there is addition of one molecule of alkylene oxide per NH group in a stoichiometric reaction which is carried out preferably in water, which is normally the best solvent for the starting amines, or in an aqueous medium and, normally, at elevated temperatures, for example from 50° to 130° C., in particular 70° to 120° C., under a pressure of, for example, from 1.1 to 10 bar, in particular 2 to 5 bar, for example in an autoclave. Examples of alcohols and/or acids which can be present in the reaction medium alone or, preferably, together with water as solvent or reaction promoter are $C_1$–$C_4$-alkanols such as those mentioned above under (a), and conventional mineral acids, eg. hydrochloric acid or sulfuric acid, or conventional carboxylic acids, eg. acetic acid.

In the second stage, after removal of water and acids and, where appropriate, alcohols if they are not required as solvent or diluent in this stage, a conventional neutral or basic catalyst is added. Suitable and preferred basic catalysts are, in particular, alkali metal hydroxides such as NaOH and KOH and alkali metal alcoholates such as sodium or potassium methanolate, ethanolate, isopropoxide and tert-butoxide. Examples of neutral catalysts which may be mentioned are layer compounds such as unmodified or modified hydrotalcite. The second stage is, as a rule, carried out at elevated temperatures of, for example, from 70° to 180° C., in particular 90° to 150° C., under similar pressures as in the first stage, for example also in an autoclave.

Water and acids and, where appropriate, alcohols are removed before the second stage is carried out either by azeotropic distillation using the solvent or diluent added according to the invention or by distillation under reduced pressure before addition of the solvent or diluent or by distillation under reduced pressure after addition of the solvent or diluent, it being possible to add the latter before, during or after the first stage and it being necessary for the latter to have a sufficiently high boiling point.

It is possible by the process according to the invention to prepare alkoxylates of oligo- or polyamines which have any number of alkylene oxide units per original NH group. Suitable and preferred in this connection are from 3 to 300, in particular 4 to 200, especially 10 to 100, alkylene oxide units per original NH group.

It is possible in the presence of the solvent or diluent which is added according to the invention to control the second stage of the alkoxylation considerably better, because the viscosity problems which otherwise occur are avoided. In particular, the reaction times are considerably shorter.

On removal of the water by azeotropic distillation before carrying out the second stage, the removal of water takes place considerably faster than on removal of water from, for example, the melt, and is virtually complete. It was particularly surprising that relatively apolar and aprotic solvents such as those from group (f) are suitable for bringing about the required removal of water from highly polar compounds, namely the appropriate amino alcohols from the first alkoxylation stage.

The products obtained by the process according to the invention can be used, in particular, for breaking crude oil emulsions. In this connection, the products which still contain the solvents or diluents used in many cases break crude oil emulsions even better than do similar products which have been prepared without the described solvents or diluents and to which such agents have been subsequently added. Such a synergistic effect has been detected on mixing similar, commercially available alkoxylated oligo- or polyamines, which have been prepared without the described solvents or diluents, with said solvents or diluents. The present application therefore likewise relates to the use of such alkoxylated oligo- or polyamines which still contain the solvents or diluents used according to the invention to break crude oil emulsions.

EXAMPLES

Example 1a

Monoalkoxylation of a polyethyleneimine in water (first stage) and removal of water by azeotropic distillation after addition of xylene 43 g of a polyethyleneimine with a weight average molecular weight of about 20,000 were introduced together with 43 g of water into an autoclave. Then, while stirring at 90°–100° C. under max. 4 bar, 58 g of propylene oxide were added over the course of 30 min. After stirring at this temperature for a further 1 h, the mixture was cooled to about 80° C., 20 g of 50% by weight aqueous KOH solution and 100 g of xylene were added, and all the water was removed by azeotropic distillation.

Example 1b

Further alkoxylation (second stage) in the presence of xylene

The precursor from Example 1a was reacted with about 2610 g of propylene oxide in an autoclave at 130°–140° C. under about 4.5 bar. The reaction time for this was 1230 min.

Comparative Example A

Examples 1a and 1b were repeated without adding xylene before the second stage. The water was in this case removed by distillation under reduced pressure (down to about 10 mbar) at 120° C. The reaction time in this second stage was 3600 min.

Example 2a

Monoalkoxylation of a polyethyleneimine in water (first stage)

43 g of a polyethyleneimine with a weight average molecular weight of about 20,000 were introduced together with 43 g of water into an autoclave. Then, while stirring at 90°–100° C. under max. 4 bar, 58 g of propylene oxide were added over the course of 30 min. After stirring at this temperature for 1 h, 20 g of 50% by weight aqueous KOH solution were added. The water was removed completely by distillation under reduced pressure (down to about 10 mbar) raising the temperature to 120° C. over the course of 5 h.

Example 2b

Further alkoxylation (second stage) in the presence of tetrahydrofuran

The precursor from Example 2a, which had been cooled to 60° C., was mixed with 100 g of tetrahydrofuran and reacted with further propylene oxide as in Example 1b. The reaction time in this case was 1190 min.

Example 2c
Further alkoxylation (second stage) in the presence of N,N-dibutylformamide The precursor from Example 2a, which had been cooled to 60° C., was mixed with 100 g of N,N-dibutylformamide and reacted with further propylene oxide as in Example 1b. The reaction time in this case was 1250 min.

Example 3a
Monoalkoxylation of a polyethyleneimine in water and polypropylene glycol (first stage)

43 g of a polyethyleneimine with a weight average molecular weight of about 20,000 were introduced together with 43 g of water and 50 g of a polypropylene glycol with an average molecular weight of about 600 into an autoclave. Then, while stirring at 90°–100° C. under max. 4 bar, 58 g of propylene oxide were added over the course of 30 min. After stirring at this temperature for a further 1 h, the mixture was cooled to about 80° C., 20 g of 50% by weight aqueous KOH solution were added, and all the water was removed under reduced pressure (down to about 10 mbar) at temperatures up to 120° C.

Example 3b
Further alkoxylation (second stage) in the presence of polypropylene glycol The precursor from Example 3a was reacted with further propylene oxide as in Example 1b. The reaction time in this case was 1300 min.

Example 4a
Monoalkoxylation of a polyethyleneimine in water and triethanolamine (first stage)

Example 3a was repeated with the difference that 50 g of triethanolamine were employed in place of the polypropylene glycol.

Example 4b
Further alkoxylation (second stage) in the presence of triethanolamine The precursor from Example 4a was reacted with further propylene oxide as in Example 1b. The reaction time in this case was 1260 min.

We claim:

1. A process for preparing alkoxylates of oligoamines or polyamines, comprising:
   reacting the NH groups of an oligoamine or a polyamine with one equivalent of an alkylene oxide in the presence of water and, optionally, an alcohol, acid or a mixture thereof in the absence of a neutral or basic catalyst, to produce an alkoxylate;
   removing the water and acid;
   adding an organic solvent or diluent or a mixture thereof selected from the group consisting of:
      (a) alcohols and phenols and their alkoxylates,
      (b) polyalcohols containing ethylene oxide, propylene oxide, butylene oxide units or a mixture thereof,
      (c) N-substituted caboxamides,
      (d) alkanolmonoamines and alkanolpolyamines and their alkoxylates,
      (e) other alkoxylates of oligoamines or polyamines,
      (f) aromatic hydrocarbons,
      (g) aliphatic hydrocarbons,
      (h) ethers and
      (i) sulfones or sulfoxides; and
   reacting the alkoxylate with an alkylene oxide in the presence of a neutral or basic catalyst to produce a polyalkoxylate.

2. A process as claimed in claim 1, wherein the organic solvent or diluent is added in an amount of from 2 to 400 parts by weight, based on the weight of the alkoxylate.

3. A process as claimed in claim 1, wherein the organic solvent or diluent is selected from the group consisting of (b), (c), (d), (f) and (h).

4. A process as claimed in claim 1, where polyalkylenepolyamines with 3 to 10 nitrogen atoms per molecule, polyvinylamines with a weight average molecular weight of from 600 to 10,000,000 or polyethyleneimines with a weight average molecular weight of from 2000 to 50,000 are employed as the oligoamine or polyamine.

5. A process as claimed in claim 1, where the alkylene oxide is selected from the group consisting of ethylene oxide, propylene oxide, butylene oxide and mixtures thereof.

6. A method for breaking oil emulsions, comprising adding the polyalkoxylate prepared as claimed in claim 1 which still comprises the organic solvent or diluent to an oil emulsion.

* * * * *